United States Patent
Barrow-Williams et al.

(10) Patent No.: US 9,649,441 B2
(45) Date of Patent: May 16, 2017

(54) INJECTION DEVICE (BAYONET CAP REMOVAL)

(75) Inventors: Timothy Donald Barrow-Williams, St. Albans (GB); Douglas Ivan Jennings, Royston (GB)

(73) Assignee: Cilag gmBh International, Landis, Gyrstrasse 1 (CH)

( * ) Notice: Subject to any disclaimer, the term of this patent is extended or adjusted under 35 U.S.C. 154(b) by 487 days.

(21) Appl. No.: 11/910,531

(22) PCT Filed: Mar. 21, 2006

(86) PCT No.: PCT/GB2006/001017
§ 371 (c)(1),
(2), (4) Date: May 29, 2008

(87) PCT Pub. No.: WO2006/106290
PCT Pub. Date: Oct. 12, 2006

(65) Prior Publication Data
US 2008/0312602 A1    Dec. 18, 2008

(30) Foreign Application Priority Data
Apr. 6, 2005    (GB) .................................. 0507014.9

(51) Int. Cl.
*A61M 5/32*    (2006.01)
*A61M 5/20*    (2006.01)
*A61M 5/31*    (2006.01)

(52) U.S. Cl.
CPC ........ *A61M 5/2033* (2013.01); *A61M 5/3202* (2013.01); *A61M 5/3204* (2013.01);
(Continued)

(58) Field of Classification Search
CPC .............. A61M 5/2033; A61M 5/3204; A61M 5/3287; A61M 5/3202; A61M 2005/3215
(Continued)

(56) References Cited

U.S. PATENT DOCUMENTS 1,845,036 A    2/1932    Busher
2,019,382 A    10/1935   Aronson
(Continued)

FOREIGN PATENT DOCUMENTS

CH    518102 A    1/1972
CN    2059579 U   7/1990
(Continued)

OTHER PUBLICATIONS

International Search Report dated Sep. 5, 2005; International Application No. PCT/GB2005/002117.
(Continued)

*Primary Examiner* — Bhisma Mehta
*Assistant Examiner* — Brandy S Lee

(57) ABSTRACT

An injection device 110 is described having a housing 112 and a housing closure means 130. The injection device 110 houses a syringe 114 having a needle 118 which is sealed by a boot 117. The housing closure means 130 is arranged so that the boot 117 can be connected to the housing closure means 130 simply, but cannot be removed from the housing closure means 130. The housing 112 and housing closure means 130 are arranged so that upon rotation of the housing closure means 130, the housing closure means 130 member first rotates relative to the housing and then moves away from the housing. The injection device is simple to use and manufacture.

6 Claims, 3 Drawing Sheets

(52) U.S. Cl.
CPC .............. *A61M 2005/3117* (2013.01); *A61M 2005/3118* (2013.01); *A61M 2005/3215* (2013.01)

(58) Field of Classification Search
USPC ................................. 604/192, 198, 195, 110
See application file for complete search history.

(56) References Cited

U.S. PATENT DOCUMENTS

| | | | |
|---|---|---|---|
| 2,147,616 A | 2/1939 | Chaput | |
| 2,295,849 A | 9/1942 | Kayden | |
| 2,531,267 A | 11/1950 | Harisch | |
| 2,764,977 A | 10/1956 | Ferguson | |
| 2,828,742 A | 4/1958 | Ashkenaz | |
| 2,854,975 A | 10/1958 | Cohen | |
| 3,076,455 A | 2/1963 | McConnaughey et al. | |
| 3,131,692 A | 5/1964 | Love | |
| 3,320,955 A | 5/1967 | Sarnoff | |
| 3,329,146 A | 7/1967 | Waldman | |
| 3,543,603 A | 12/1970 | Gley | |
| 3,656,472 A | 4/1972 | Moura | |
| 3,702,608 A | 11/1972 | Tibbs | |
| 3,742,948 A | 7/1973 | Post et al. | |
| 3,797,488 A | 3/1974 | Hurschman et al. | |
| 3,797,489 A | 3/1974 | Sarnoff | |
| 3,880,163 A | 4/1975 | Ritterskamp | |
| 3,976,069 A | 8/1976 | Ong | |
| 4,165,739 A | 8/1979 | Doherty et al. | |
| 4,180,070 A | 12/1979 | Genese | |
| 4,185,628 A | 1/1980 | Kopfer | |
| 4,194,505 A | 3/1980 | Schmitz | |
| 4,222,380 A | 9/1980 | Terayama | |
| 4,231,368 A | 11/1980 | Becker | |
| 4,236,516 A | 12/1980 | Nilson | |
| 4,299,238 A | 11/1981 | Baidwan et al. | |
| 4,333,459 A | 6/1982 | Becker | |
| 4,378,015 A | 3/1983 | Wardlaw | |
| 4,394,863 A | 7/1983 | Bartner | |
| 4,403,989 A | 9/1983 | Christensen et al. | |
| 4,407,283 A | 10/1983 | Reynolds | |
| 4,425,120 A | 1/1984 | Sampson et al. | |
| 4,430,082 A | 2/1984 | Schwabacher | |
| 4,521,237 A | 6/1985 | Logothetis | |
| 4,561,856 A | 12/1985 | Cochran et al. | |
| 4,627,835 A | 12/1986 | Fenton, Jr. | |
| 4,636,201 A | 1/1987 | Ambrose et al. | |
| 4,639,250 A | 1/1987 | Rycroft | |
| 4,642,099 A | 2/1987 | Phillips et al. | |
| 4,676,530 A | 6/1987 | Nordgren et al. | |
| 4,717,383 A | 1/1988 | Phillips et al. | |
| 4,744,786 A | 5/1988 | Hooven et al. | |
| 4,787,891 A | 11/1988 | Levin et al. | |
| 4,874,383 A | 10/1989 | McNaughton | |
| 4,874,384 A | 10/1989 | Nunez | |
| 4,929,232 A | 5/1990 | Sweeney et al. | |
| 4,969,870 A | 11/1990 | Kramer et al. | |
| 4,988,339 A | 1/1991 | Vadher | |
| 5,009,646 A | 4/1991 | Sudo et al. | |
| 5,026,349 A | 6/1991 | Schmitz et al. | |
| 5,057,079 A | 10/1991 | Tiemann et al. | |
| 5,092,842 A | 3/1992 | Bechtold et al. | |
| 5,098,400 A | 3/1992 | Crouse et al. | |
| 5,112,119 A | 5/1992 | Cooke et al. | |
| 5,114,406 A | 5/1992 | Gabriel et al. | |
| 5,122,119 A | 6/1992 | Lucas | |
| 5,137,516 A * | 8/1992 | Rand et al. | 604/136 |
| 5,141,496 A | 8/1992 | Dalto et al. | |
| 5,147,325 A | 9/1992 | Mitchell et al. | |
| 5,156,599 A | 10/1992 | Ranford et al. | |
| 5,176,643 A | 1/1993 | Kramer et al. | |
| 5,190,526 A | 3/1993 | Murray et al. | |
| 5,242,416 A | 9/1993 | Hutson | |
| 5,250,026 A | 10/1993 | Ehrlich et al. | |
| 5,250,037 A * | 10/1993 | Bitdinger | 604/192 |
| 5,263,933 A | 11/1993 | Novacek et al. | |
| 5,267,963 A | 12/1993 | Bachynsky | |
| 5,271,744 A | 12/1993 | Kramer et al. | |
| 5,295,965 A | 3/1994 | Wilmot | |
| 5,300,030 A | 4/1994 | Crossman et al. | |
| 5,312,364 A | 5/1994 | Jacobs | |
| 5,330,081 A | 7/1994 | Davenport | |
| 5,330,430 A | 7/1994 | Sullivan | |
| 5,356,395 A | 10/1994 | Chen | |
| 5,358,489 A | 10/1994 | Wyrick | |
| 5,364,369 A | 11/1994 | Reynolds | |
| 5,368,577 A | 11/1994 | Teoh et al. | |
| 5,372,586 A | 12/1994 | Haber et al. | |
| 5,391,151 A | 2/1995 | Wilmot | |
| 5,405,362 A | 4/1995 | Kramer et al. | |
| 5,411,488 A | 5/1995 | Pagay et al. | |
| 5,425,715 A | 6/1995 | Dalling et al. | |
| 5,451,210 A | 9/1995 | Kramer et al. | |
| 5,478,316 A | 12/1995 | Bitdinger et al. | |
| 5,480,387 A | 1/1996 | Gabriel et al. | |
| 5,487,732 A | 1/1996 | Jeffrey | |
| 5,489,256 A | 2/1996 | Adair | |
| 5,503,627 A | 4/1996 | McKinnon et al. | |
| 5,514,097 A | 5/1996 | Knauer | |
| 5,520,653 A | 5/1996 | Reilly et al. | |
| 5,540,660 A | 7/1996 | Jenson et al. | |
| 5,540,666 A | 7/1996 | Barta et al. | |
| 5,540,709 A | 7/1996 | Ramel et al. | |
| 5,567,160 A | 10/1996 | Massino | |
| 5,569,191 A | 10/1996 | Meyer | |
| 5,569,192 A | 10/1996 | van der Wal | |
| 5,575,777 A | 11/1996 | Cover et al. | |
| 5,599,302 A | 2/1997 | Lilley et al. | |
| 5,599,309 A | 2/1997 | Marshall et al. | |
| 5,607,395 A | 3/1997 | Ragsdale et al. | |
| 5,609,577 A | 3/1997 | Haber et al. | |
| 5,609,584 A * | 3/1997 | Gettig et al. | 604/535 |
| 5,611,785 A | 3/1997 | Mito et al. | |
| 5,637,094 A | 6/1997 | Stewart, Jr. et al. | |
| 5,645,536 A | 7/1997 | Whisson | |
| 5,647,845 A | 7/1997 | Haber et al. | |
| 5,649,912 A | 7/1997 | Peterson | |
| 5,658,259 A | 8/1997 | Pearson et al. | |
| 5,665,071 A | 9/1997 | Wyrick | |
| 5,681,291 A | 10/1997 | Galli | |
| 5,697,908 A | 12/1997 | Imbert | |
| 5,702,367 A | 12/1997 | Cover et al. | |
| 5,704,911 A | 1/1998 | Parsons et al. | |
| 5,709,662 A | 1/1998 | Olive et al. | |
| 5,713,866 A | 2/1998 | Wilmot | |
| 5,748,316 A | 5/1998 | Wakabayashi et al. | |
| 5,779,668 A | 7/1998 | Grabenkort | |
| 5,779,677 A | 7/1998 | Frezza | |
| 5,807,334 A | 9/1998 | Hodosh et al. | |
| 5,817,058 A | 10/1998 | Shaw | |
| 5,827,262 A | 10/1998 | Neftel et al. | |
| 5,843,036 A | 12/1998 | Olive et al. | |
| 5,855,839 A | 1/1999 | Brunel | |
| 5,865,795 A | 2/1999 | Schiff et al. | |
| 5,865,804 A | 2/1999 | Bachynsky | |
| 5,868,711 A | 2/1999 | Kramer et al. | |
| 5,879,327 A | 3/1999 | Moreau DeFarges et al. | |
| 5,913,843 A | 6/1999 | Jentzen | |
| 5,928,205 A | 7/1999 | Marshall | |
| 5,954,738 A | 9/1999 | LeVaughn et al. | |
| 5,957,897 A | 9/1999 | Jeffrey | |
| 5,960,797 A | 10/1999 | Kramer et al. | |
| 5,997,513 A | 12/1999 | Smith et al. | |
| 6,007,515 A | 12/1999 | Epstein et al. | |
| 6,015,438 A | 1/2000 | Shaw | |
| 6,017,330 A | 1/2000 | Hitchins et al. | |
| 6,036,675 A | 3/2000 | Thorne et al. | |
| 6,045,534 A | 4/2000 | Jacobsen et al. | |
| 6,068,614 A | 5/2000 | Kimber et al. | |
| 6,077,247 A | 6/2000 | Marshall et al. | |
| 6,083,197 A | 7/2000 | Umbaugh | |
| 6,086,562 A | 7/2000 | Jacobsen et al. | |
| 6,090,070 A | 7/2000 | Hager et al. | |
| 6,090,078 A | 7/2000 | Erskine | |
| 6,090,897 A | 7/2000 | Akasaki et al. | |

(56) References Cited

U.S. PATENT DOCUMENTS

| | | |
|---|---|---|
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Greco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,585,702 B1 * | 7/2003 | Brunel ............ 604/263 |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 * | 2/2004 | Weekes et al. ............ 604/197 |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell-Montalvo et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 8,932,264 B2 | 1/2015 | DeSalvo |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |

(56) References Cited

U.S. PATENT DOCUMENTS

| | | |
|---|---|---|
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0233502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0257193 A1 | 9/2014 | Bostrom et al. |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |

(56) References Cited

FOREIGN PATENT DOCUMENTS

| | | |
|---|---|---|
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0389938 | 10/1990 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 | 11/1988 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |

(56) References Cited

FOREIGN PATENT DOCUMENTS

| | | |
|---|---|---|
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |
| WO | WO 2012/000835 A1 | 1/2012 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 2006081640.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.

(56) References Cited

OTHER PUBLICATIONS

International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
Australian Search Report dated Dec. 5, 2007; International Application No. SG-200608165-7.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
International Search Report dated Feb. 26, 2008; International Application No. PCT/GB2007/004335.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
European Search Report dated Aug. 3, 2011; Application No. 11170040.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
European Search Report dated Apr. 28, 2015; Application No. 15153304.9.
International Search Report dated Jan. 29, 2015; International Application No. PCT/EP2014/062167.

(56) References Cited

OTHER PUBLICATIONS

International Preliminary Report dated Dec. 15, 2015; International Application No. PCT/EP2014/062163.
International Preliminary Report dated Dec. 15, 2015; International Application No. PCT/EP2014/062166.

* cited by examiner

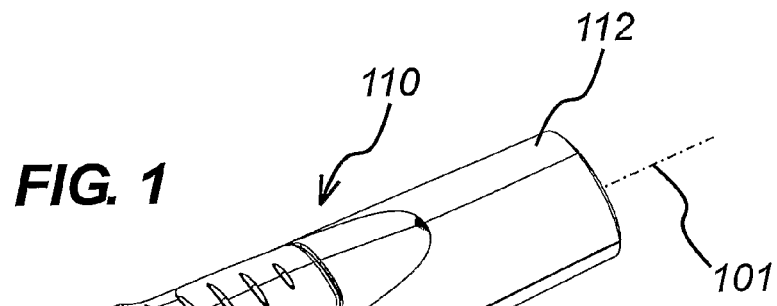
FIG. 1
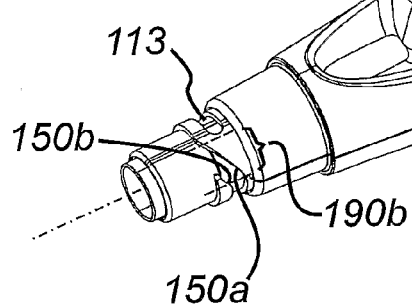
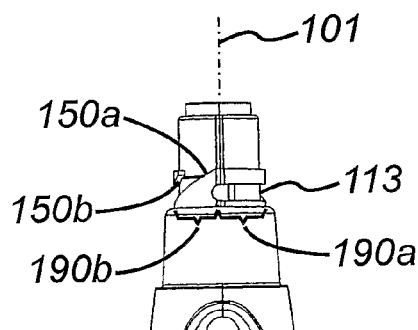
FIG. 2
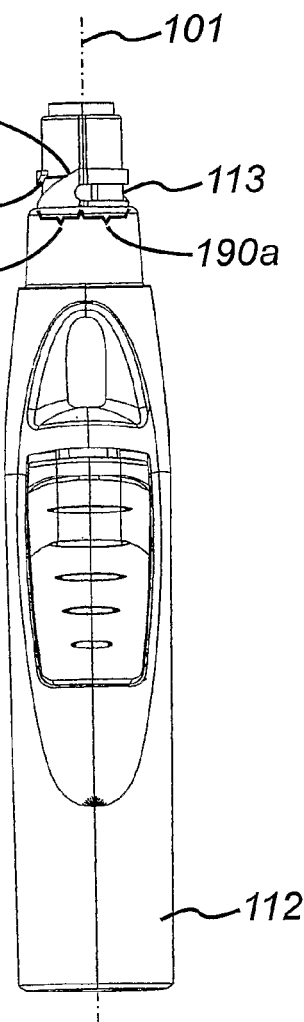

INJECTION DEVICE (BAYONET CAP REMOVAL)

FIELD OF THE INVENTION

The present invention relates to an injection device of the type that receives a syringe and includes a cap over a dispensing aperture of the injection device.

BACKGROUND OF THE INVENTION

Injection devices of a general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with sealed hypodermic syringes which typically have a hermetically sealed cover or "boot" that covers the hypodermic needle and maintains the sterility of the syringe contents. Naturally, it is necessary to maintain the sterility of the syringe contents up to the point of administration, which means that for devices that are designed to be disposable, the boot must be removed with the syringe inside the injection device.

In previously known injection devices, the action required to remove the boot from the syringe entails either pulling the boot away from the syringe or twisting the boot and, at the same time, pulling it away from the syringe.

If the injection devices are used by patients having rheumatoid arthritis or elderly or weak patients, it is difficult for the patient to remove the boot from the syringe prior to its use. In addition, the boots are small and fiddly to grip for all users but particularly for users who have poor flexibility in their joints or limited manual dexterity. Since the boot of the syringe may be positioned inside the housing, there may also be limited access to the boot.

Co-pending United Kingdom patent application no. 0412051.5, the contents of which is incorporated herein by reference, describes a cap for an injection device that connects to the boot of the syringe so that removal of the housing closure member from the housing causes removal of the boot from the syringe.

In certain types of syringe, for example a Bünder ReadyJect™ type syringe, the boot must be twisted to break a frangible joint before it can be pulled off. An inexperienced user of the injection device might attempt to pull the cap of the injection device off without first twisting. This could lead to either the boot pulling out of the cap of the injection device and remaining on the syringe or the syringe components separating. In either case, the user will not be able to use the injection device to successfully deliver a drug product.

SUMMARY OF THE INVENTION

The injection devices of the present invention are designed to deal with these problems.

In view of the foregoing and in accordance with the present invention, there is provided an injection device comprising:
  a housing adapted to receive a syringe having a discharge nozzle and a boot that covers its discharge nozzle, the housing having a longitudinal axis and including a first guide; and
  a housing closure member including a second guide;
  wherein the first guide and the second guide are arranged so that rotation of the housing closure member relative to the housing causes the housing closure member first to rotate relative to the housing and then to move away from the housing, wherein the housing closure member further comprising means for connecting to the boot of the syringe so that removal of the housing closure member from the housing causes removal of the boot from the syringe.

Hence, the boot is first twisted to break a frangible joint holding it the syringe before being pulled off. This way, an inexperienced user of the injection device cannot pull the cap of the injection device off without first twisting.

Preferably, one of the first guide and the second guide comprises a slot and the other of the first guide and the second guide comprises a protrusion for communicating with the slot.

The slot can have a first section which runs in a direction perpendicular to a first axis of the housing and a second section which turns away from the first section towards the direction of the first axis.

Preferably, the protrusion is moulded from the same material as the housing closure means.

In one embodiment of the invention, one of the housing and the housing closure member has a second slot and the other of the housing and the housing closure member has a second protrusion for communicating with the second slot.

The injection device may further comprise an external grip feature with which a user can grip the housing closure member.

Advantageously, the means for connecting may comprise a plurality of splines.

Preferably, the plurality of splines is arranged around the internal diameter of a cylinder mounted on the housing closure means.

The splines may be mounted on the cylinder such that the angle formed between each spline and a radius of the cylinder is less than 90 degrees. Upon connecting the boot of the syringe to the housing closure member and rotating the housing closure member, the splines rotate the boot of the syringe relative to the discharge nozzle.

BRIEF DESCRIPTION OF THE DRAWINGS

The invention will now be described by way of example with reference to the accompanying drawings, in which:

FIG. 1 shows a perspective view of an injection device according to the present invention with the housing closure member removed;

FIG. 2 shows a plan view of the injection device of FIG. 1;

DETAILED DESCRIPTION OF THE DRAWINGS

Figure 3:
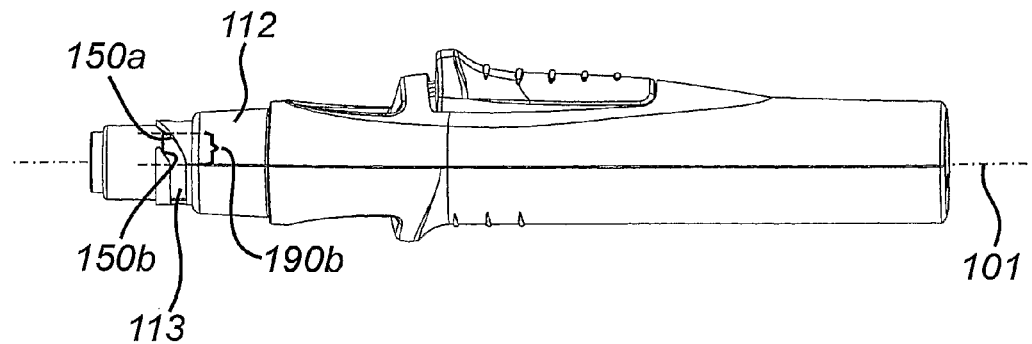
FIG. 3 shows a side view of the injection device of FIG. 1.
Figure 4:
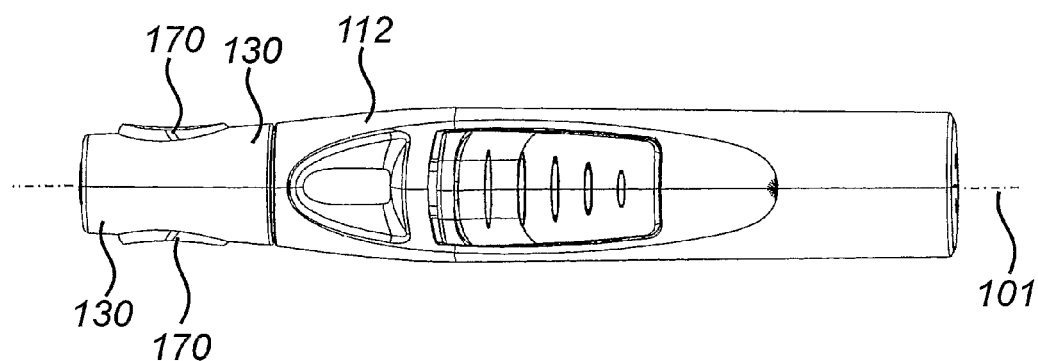
FIG. 4 shows a plan view of the injection device of FIGS. 1 to 3, with the housing closure member in place.
Figure 5:
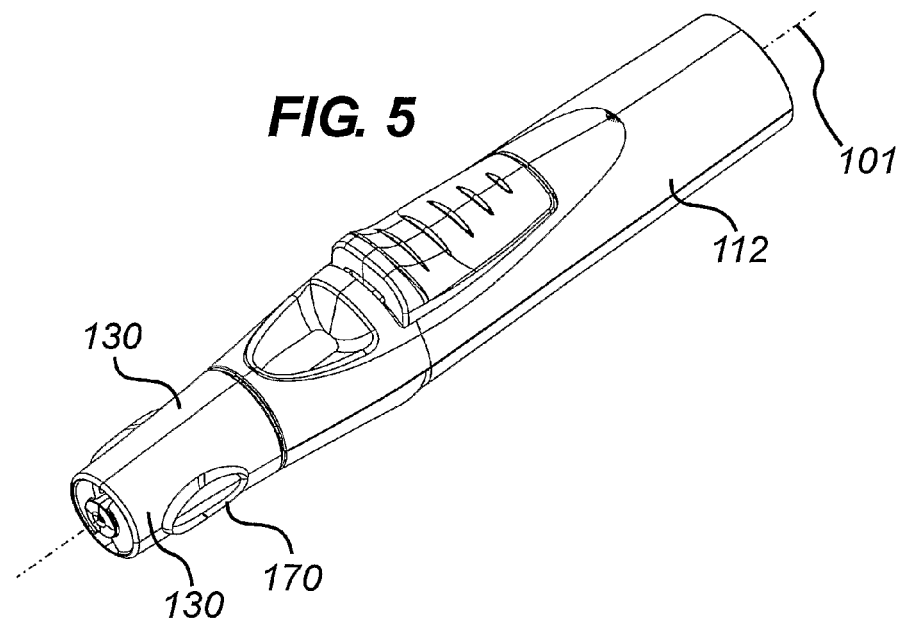
FIG. 5 shows a perspective view of the injection device of FIG. 4.

FIGS. 1 to 5 and 9 show an injection device 110 according to a first embodiment of the present invention. The injection device 110 has an injection device housing 112.

The injection device 110 has a longitudinal axis 101.

The housing 112 contains a hypodermic syringe 114 of conventional type, including a syringe body 116 defining a reservoir and terminating at one end in a hypodermic needle 118. The syringe 114 has a hermetically sealed cover or boot 117 that covers the hypodermic needle 118 and maintains the sterility of the syringe contents. The boot 117 is generally formed of a soft rubber or plastics material. The boot 117 comprises a plurality of flat faces 165 formed on its outer surface about its circumference.

Whilst the syringe illustrated is of hypodermic type, this need not necessarily be so. Transcutaneous or ballistic dermal and subcutaneous syringes may also be used with the injection device of the present invention.

The injection device is further provided with a cap 130. As is best seen from FIGS. 1 to 3 and 6, the cap is retained on the housing 112 by a slot 113 on the housing 112, and a corresponding indentation 131 on the inside of the cap 130.

In a first section 190a, the slot 113 is formed around the housing 112 tangential about the longitudinal axis 101 of the housing 112. In a second section 190b, the slot 113 is formed with two opposing camming surfaces 150a and 150b which are curved in such a way that the slot is directed away from the its tangential direction about the longitudinal axis to a direction along the longitudinal axis 101 of the housing 112.

Figure 6:
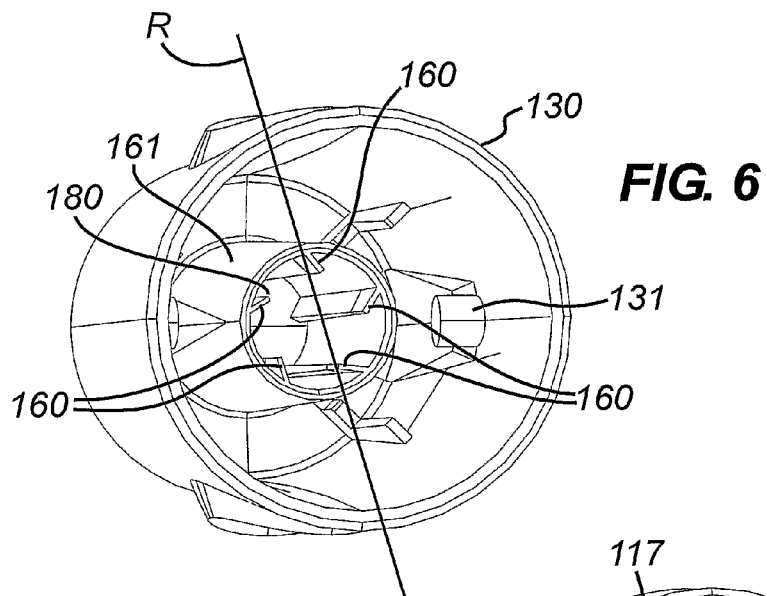
FIG. 6 shows a perspective view of a housing closure member for use in an injection device according to an embodiment of the present invention.
Figure 7:
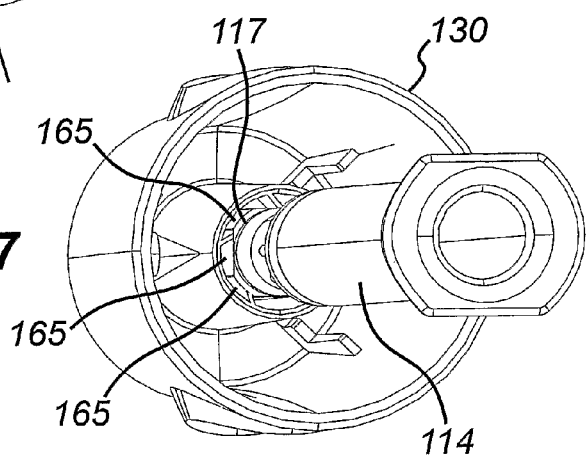
FIG. 7 shows the housing closure member of FIG. 7 when engaged with a syringe boot of a syringe used with an injection device according to an embodiment of the present invention.
Figure 8:
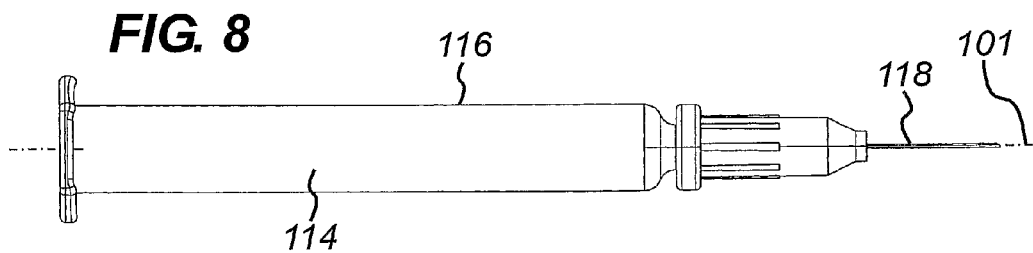
FIG. 8 shows a side view of a syringe used in the injection device according to an embodiment of the present invention.
Figure 9:
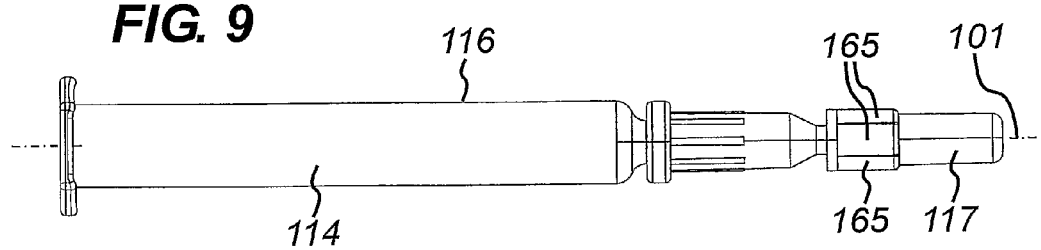
FIG. 9 shows a side view of the syringe of FIG. 8 with a syringe boot engaged with the syringe.

As can be seen from FIGS. 6 and 7, the interior of the cap 130 is provided with a plurality of splines 160. These splines 160 are arranged around an internal diameter of a cylinder 161 mounted inside the cap 130. The splines 160 are mounted on the cylinder such that the angle formed between each spline and a radius R of the cylinder 161 is less than 90 degrees. The splines 160 are dimensioned so that they flex resiliently in a direction along the radius R of the cylinder.

The exterior of the cap 130 is provided with a pair of grip formations 170. These grip formations 170 provide an element through which a user can grip the cap 130.

As can be seen from FIG. 6, the interior of the cap 130 may be provided with a support surface 180 which supports the end of the boot 117.

During manufacture of the injection device 110, the syringe 114 and boot 117 are inserted into the housing 112 as a single piece. The cap 130 is placed onto the housing such that the boot 117 is forced into the space in the cylinder 161 between the splines 160 which flex to allow insertion of the cap 130 onto the boot 117. As a result of the flexing of the splines 160, the cap 130 grips the boot 117 firmly because each spline is forced against one of the flat surfaces 165 of the boot 117. Consequently a very form grip is produced on the boot 117.

When the injection device 110 is to be used, the user holds the housing 112 with one hand, and grips the cap 130 with the other hand using the grip formations 170. The user then rotates the cap 130. In rotating the cap 130, the projection 131 of the cap 130 moves in the slot 113 of the housing 112, thereby rotating the boot 117 relative to the syringe 116. This rotational movement breaks the frangible connection between the boot 117 and the syringe 114 before any axial movement of the boot 117 relative to the syringe 116 takes place. This is because the slot is formed, in its first section 190a, circumferentially on the housing 112 solely in a direction which is tangential to the longitudinal axis 101 of the housing 112. After the frangible connection has broken, the boot 117 is free to move axially. On further rotation, the projection 131 reaches the camming surfaces 150a and 150b of the slot 113 in its second section 190b, thereby allowing the cap 130 and attached boot 117 to move in a direction along the longitudinal axis 101 of the housing 112, thereby removing the boot 117 from the syringe.

The boot 117 is held stationary within the cap 130 by the splines 160 being forced against and gripping the flat surfaces 165 of the boot 117.

The support surface 180 helps to prevent the boot 117 from being pulled away from the syringe 114 at an angle, by maintaining the axial alignment of the boot 117 within the cap 130.

The present invention provides a simple and effective way of solving the problems of the prior art devices.

In particular, when used with the type of syringe in which the boot must be twisted to break a frangible joint before it can be pulled off, the present invention prevents pulling the cap of the injection device off without first twisting. This way, the boot is not pulled out of the cap of the injection device, does not remain on the syringe and does not cause the syringe components to separate.

It will of course be understood that the present invention has been described above purely by way of example and modifications of detail can be made within the scope of the invention.

The invention claimed is:

1. An injection device comprising:
   a housing adapted to receive a syringe having a needle and a boot that covers its needle, the housing having a longitudinal axis and including a first guide; and
   a housing closure member including means for attaching the closure member to the housing comprising a second guide, wherein the first and second guides are attached to each other;
   wherein the first guide and the second guide detach from each other so as to detach the housing closure member from the housing and are arranged so that rotation of the housing closure member relative to the housing causes the housing closure member first to move relative to the housing solely through rotation in a direction tangential to the longitudinal axis of the housing and then to move away from the housing in a direction parallel to the longitudinal axis of the housing,
   wherein the housing closure member further comprises means for connecting to the boot of the syringe so that removal of the housing closure member from the housing causes removal of the boot from the syringe,
   wherein the means for connecting comprises a plurality of splines moulded from the same material as the housing closure member,
   wherein, upon connecting the boot of the syringe to the housing closure member and rotating the housing closure member, the splines rotate the boot of the syringe relative to the needle,
   wherein one of the first guide and the second guide comprises a slot and the other of the first guide and the second guide comprises a protrusion for communicating with the slot, wherein the slot has a first section which runs in a direction perpendicular to the longitudinal axis, and a second section which turns away from the first section towards the direction of the longitudinal axis.

2. An injection device according to claim 1, wherein the protrusion is molded from the same material as the housing closure member.

3. An injection device according to claim 1, wherein one of the housing and the housing closure member has a second slot and the other of the housing and the housing closure member has a second protrusion for communicating with the second slot.

4. An injection device according to claim 1 further comprising an external grip feature with which a user can grip the housing closure member.

5. An injection device according to claim 1, wherein the plurality of splines are arranged around an internal diameter of a cylinder mounted on the housing closure member.

6. An injection according to claim 5, wherein the splines are counted on the cylinder such that an angle formed between each spline and a radius of the cylinder is less than 90 degrees.

* * * * *